Figure 1:
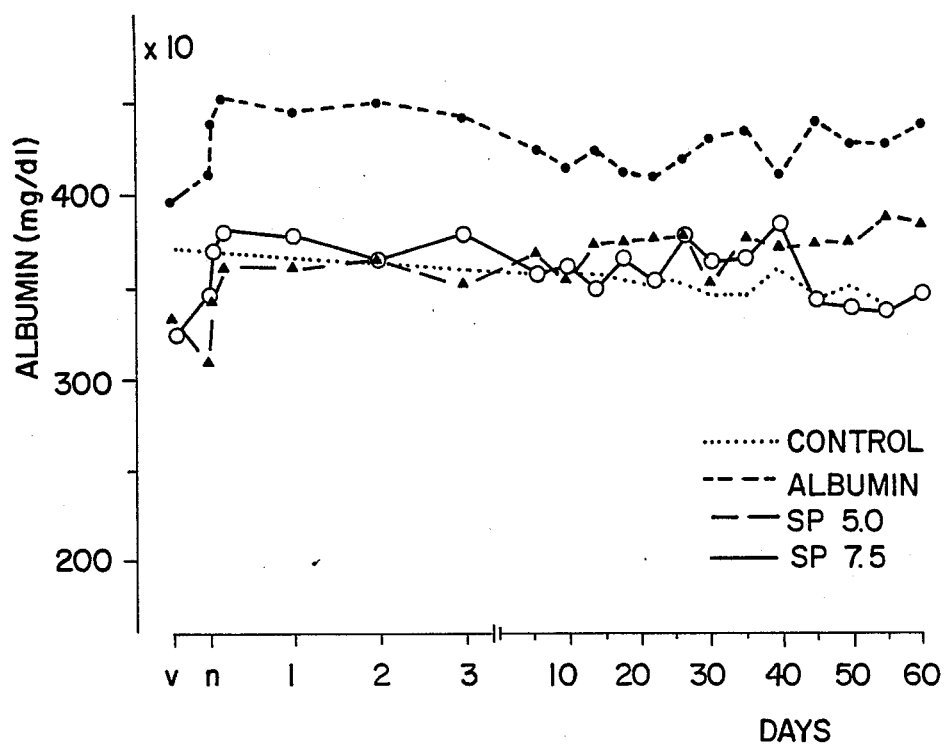
Figure 2:
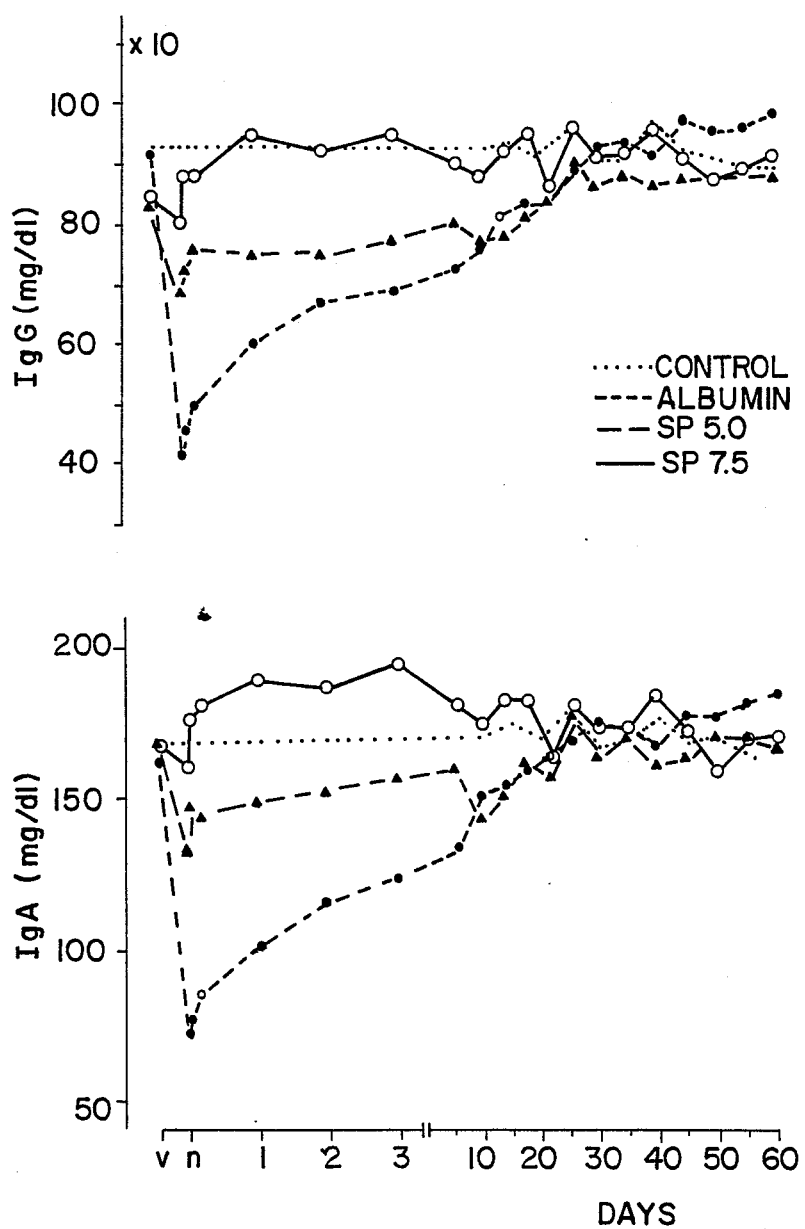
Figure 3:
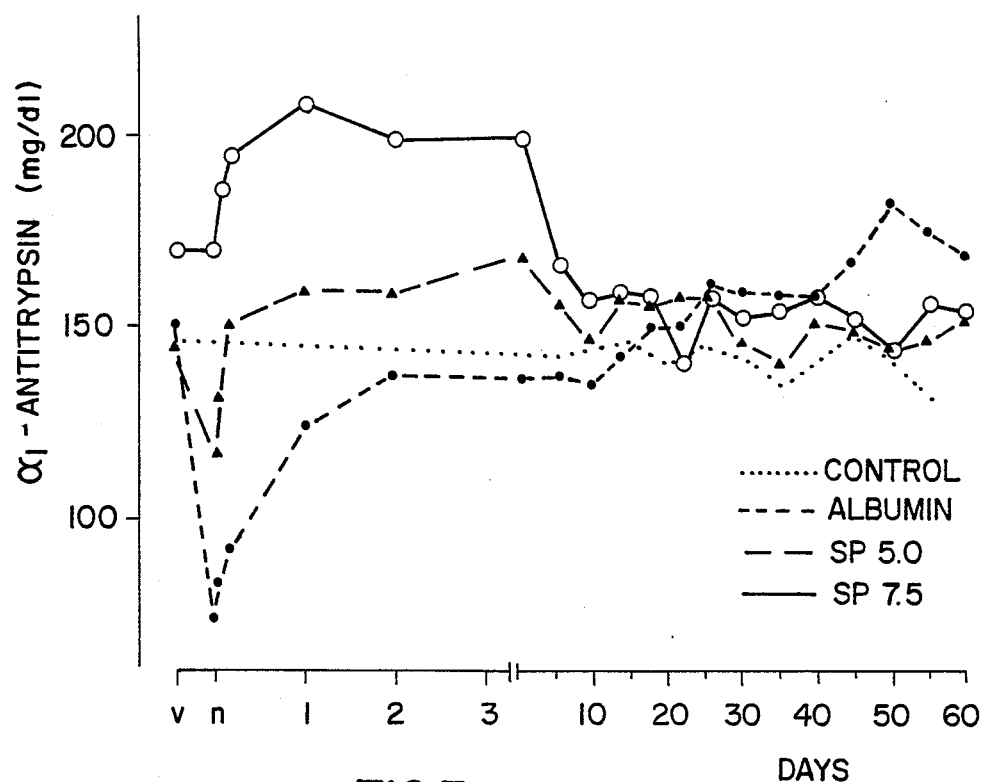
Figure 4:
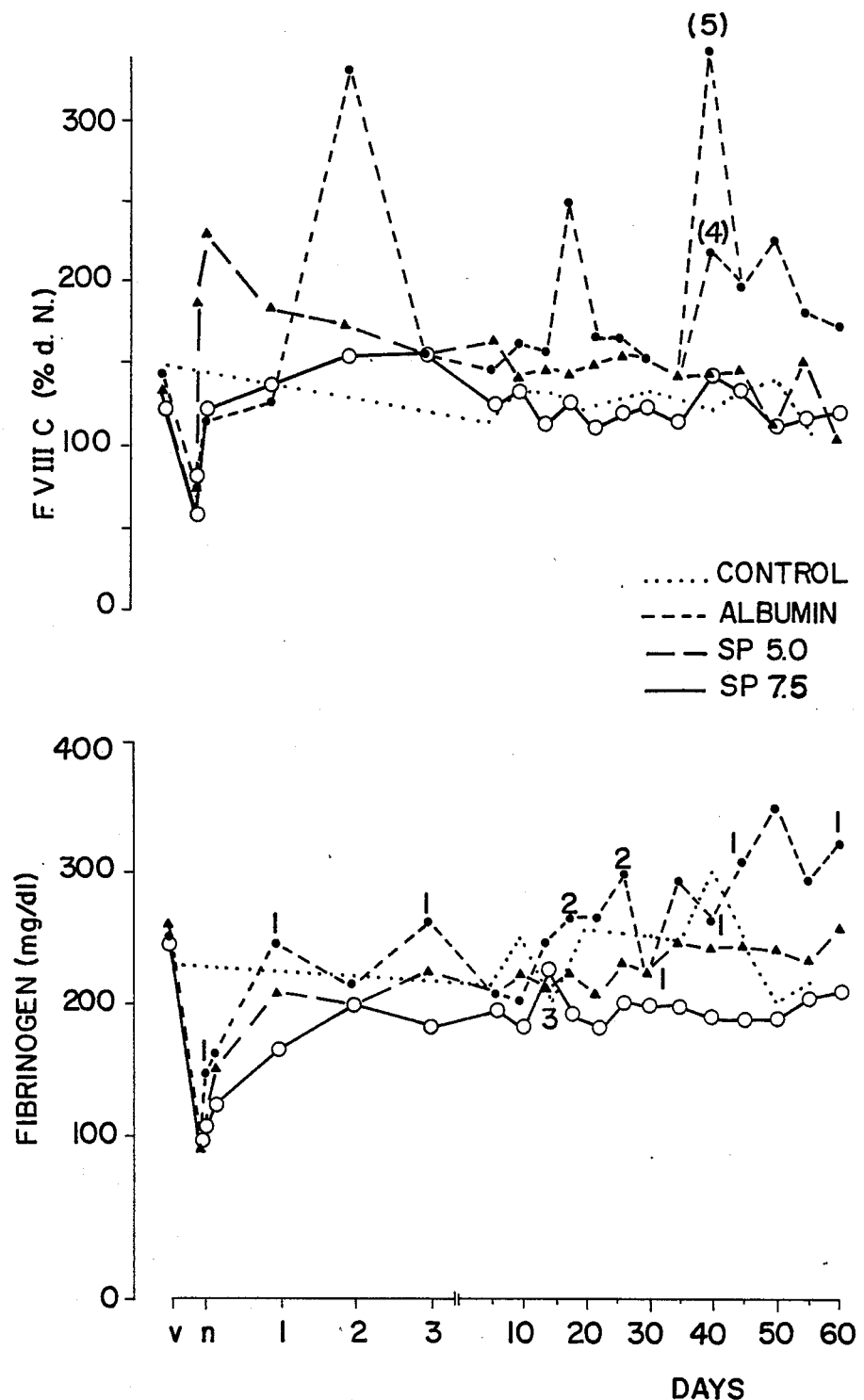

United States Patent [19]

Kotitschke

[11] Patent Number: 4,900,720
[45] Date of Patent: Feb. 13, 1990

[54] REPLACEMENT OF HUMAN PLASMA USING STERILE SOLUTION OF HUMAN PLASMA PROTEINS EXCLUDING BLOOD COAGULATION FACTORS

[75] Inventor: Ronald Kotitschke, Dreieich, Fed. Rep. of Germany

[73] Assignee: Boitest Pharma GmbH, Frankfurt, Fed. Rep. of Germany

[21] Appl. No.: 34,468

[22] Filed: Apr. 6, 1987

[30] Foreign Application Priority Data

Apr. 10, 1986 [DE] Fed. Rep. of Germany ....... 3612137

[51] Int. Cl.$^4$ .................... A61K 37/02; A61K 37/04; A61K 37/62; A61K 35/16
[52] U.S. Cl. ................................. 514/21; 530/363; 530/380; 530/381; 530/382; 530/387; 530/385; 530/393; 530/394; 530/350
[58] Field of Search .................. 514/21; 424/446, 447, 424/448, 449, 491, 499, 94.67; 530/363, 380, 381, 385, 387, 350, 393, 394

[56] References Cited

U.S. PATENT DOCUMENTS

| | | | |
|---|---|---|---|
| 4,025,500 | 5/1977 | Garcia et al. | 530/387 |
| 4,170,590 | 10/1979 | Stephan et al. | 424/101 |
| 4,271,122 | 6/1981 | Strässle et al. | 424/101 |
| 4,272,523 | 6/1981 | Kotitschke et al. | 424/101 |
| 4,370,264 | 1/1983 | Kotitschke et al. | 424/101 |
| 4,503,030 | 3/1985 | Kotitschke et al. | 424/101 |
| 4,656,254 | 4/1987 | Shearer et al. | 530/380 |
| 4,697,003 | 9/1987 | Loan | 530/380 |

OTHER PUBLICATIONS

Stedeman's Medical Dictionary, pp. 1664–1671, (1982), Waverly Press, Hensyl (Editor).

Primary Examiner—Margaret Moskowitz
Assistant Examiner—Jeff Kushan
Attorney, Agent, or Firm—Sprung horn Kramer & Woods

[57] ABSTRACT

To maintain an almost unchanged plasma-protein profile in a patient subsequent to plasma exchange, the plasma-exchange medium contains the most essential human serum proteins, except for the coagulation factors, at a concentration of 75 g/l.

1 Claim, 4 Drawing Sheets

REPLACEMENT OF HUMAN PLASMA USING STERILE SOLUTION OF HUMAN PLASMA PROTEINS EXCLUDING BLOOD COAGULATION FACTORS

The invention relates to a sterile plasma-exchange medium.

Therapeutic plasmapheresis (although the nomenclature relating to plasmapheresis and plasma exchange in the literature is unfortunately not uniform, therapeutic plasmapheresis and plasma exchange are to be understood herein as referring to replacing a patient's plasma with a substitute medium) is employed to eliminate pathogenic substances from a patient's blood. The indications for exchange therapy can be quite varied (P. Reuther, D. Wiebecke, R. Rokkam, & H. G. Mertens, "Plasma-exchange treatments in neurological conditions" [in German], *Nervenarzt* 54 [1983], 151–70 and H. Borberg & P. Reuther, *Plasma-Exchange Therapy,* Stuttgart, Thieme, 1981).

Normal plasma constituents are removed along with the pathogenic substances. How many normal proteins are removed and how fast they are returned to or replaced in the body is a decisive criterion for the quality of the particular exchange medium employed.

The plasma-protein profile (the composition and concentration of the proteins in the plasma) of a healthy person represents an inherent defense system that allows for limited fluctuations in the concentration of the individual plasma constituents. The limits differ for different proteins Petralito, R. A. Mangiafico, S. Gibiino, M. A. Cuffari, M. F. Miano, & C. E. Fiore, Daily modifications of plasma fibrinogen, platelets aggregation, Howel's time, PTT, TT, and antithrombin III in normal subjects and in patients with vascular disease," *Chronobiologia* 9[1982], 195–201).

Disruption of the normal plasma-protein profile is characteristic of many diseases, and deviations from the normal plasma-protein composition can entail serious consequences for the organism. When therapeutic plasma exchange is indicated as a treatment for certain diseases, it would be desirable to maintain the normal plasma-protein profile by substituting a medium appropriate for that purpose.

The changes in the composition of the proteins (protein profile) ascribable to the use of crystalloid solutions in plasma exchange are considerable (J. B. Orlin & E. M. Berkman, "Partial plasma exchange using albumin replacement: removal and recovery of normal plasma constituents," *Blood* 56, 6 [1980], 1055–59; R. L. Volkin, T. W. Starz, A. Winkelstein, R. K. Shadduch, J. H. Lewis, U. Hasiba, & J. A. Spero, "Changes in coagulation factors, complement, immunoglobulins, and immune complex concentrations with plasma exchange," *Transfusion* 22, 1 [1982], 54–58; and M. Kuhlencordt, D. E. Vogel, C. Komm, & A. Oberdorfer, "Changes in the plasma coagulation system during plasmapheresis" [in German], *Intensivmedizin* 21, 6[1984], 305–08).

The drug most frequently employed today in therapeutic plasma exchange is an albumin solution with a protein concentration of 50 g/l. The use of albumin to replace all the other proteins removed in therapeutic plasma exchange raises an important question. Might the absence of immunoglobulins not provoke increased production of immunoglobulins that become pathologically active in patients subjected to plasma exchange? A classical indication for therapeutic plasma exchange, in fact, is immunologically dictated diseases. Depletion of the immunoglobulins due to plasma exchange could also increase the patients' risk of contracting infections. This risk has been diminished by employing fresh-frozen plasma (FFP) as a replacement medium in plasma exchange. Fresh-frozen plasma, however, has had a very high rate of side effects. As much as 16% of the patients treated have developed urticaria, and in some patients the side effects have resulted in anaphylactic shock. Repeated substitution with fresh-frozen plasma leads to cumulation of the fibrinogen concentration and hence, due to fibrinogen's relatively long half-time of 3.5 days, to an increased risk of thrombosis.

Stegmayr et al. attempted to eliminate the problem of high rates of side effects by using, instead of fresh-frozen plasma, plasma from which the cryoprecipitate had been separated (B. Stegmayr, B. Cedergren, & B. Lindquist, "Is stored liquid plasma or cryoprecipitate-poor plasma an alternative for fresh-frozen plasma as substitution in plasma exchange?" *Abstracts, International Symposium on Therapeutic Plasma Exchange and Selective Plasma Separation,* Homburg-Saar, 1985).

Other reasons for preferring plasma-protein fractions such as albumin over plasma as an exchange medium in therapeutic plasma exchange are the limited availability of compatible plasmas and the risk of transmitting hepatitis in unsterilized plasmas. On the other hand, the removal of three to five liters of plasma in one plasma exchange is responsible for a dramatic decrease in proteins with biological activities and can entail undesirable consequences for the hemostasis potential. When plasma exchange is repeated at short intervals, furthermore, the side effects can become additive. Sultan et al accordingly studied the effects of repeated plasma exchange on patients with myasthenia gravis and demonstrated that the patients were exposed to an increased risk of thrombosis when albumin solutions and lactated Ringer's solutions were used as exchange media (Y. Sultan, A. Bussel, P. Maisonneuve, M. Ponpeney, S. Sitty, & P. Gajdos, "Potential danger of thrombosis after plasma exchange in the treatment of patients with immune disease," *Transfusion* 19[1979], 588–593).

The following question is accordingly of especially significant in selecting an optimal plasma-exchange medium:

Is there a plasma-exchange medium with properties that ensure that the organism will be affected as little as possible by the exchange and that the normal plasma-protein profile will be altered as little as possible?

Theoretically, the ideal exchange medium for blood is blood, Still, its unsatisfactory keeping qualities militate against the use of whole blood for this purpose. It is also unnecessary in an exchange treatment to replace the patient's actual blood cells because the machines and equipment employed make it possible to return the originals.

In stabilizing blood and separating it into the cells and the plasma that contains the proteins, the plasma must be deep-frozen directly subsequent to harvesting because some of the proteins in the plasma are highly labile. What prevents the use of fresh-frozen plasma as the agent of choice in practical therapeutic plasma exchange are in particular the high rate of side effects and the potential for transmitting viruses. The fractionation of plasma into individual protein fractions allows the production of high-purity albumin solutions that, once specific stabilizers have been added to them, can be pasteurized. The use of pasteurized albumin solutions prevents the transmission of infectious diseases.

European Patent No. 0 014 333 describes a serum-protein solution (Biseko$^{(R)}$) sterilized with β-propriolactone and ultraviolet radiation and having a concentration of 50 g/l. This solution was tested in comparison with a 5.0% albumin exchange as an exchange medium on 5 healthy volunteers (R. Kotitschke, H. Borberg, & G. Güsken, "Long-term study of the protein profile in healthy subjects subsequent to plasma exchange" [in German], *Abstracts* and Handout Poster, 29th Annual Meeting, DAB-GTH, Homburg-Saar, E. Wenzel and P. Hellstern [1985], 23).

A 5.0% serum-protein solution leads, subsequent to plasma exchange, to definitely less of a change in the concentration of individual proteins in comparison with a 5.0% albumin solution, although the deviation continues to be definitely greater in relation to individual proteins than that of normal biological variations.

The object of the present invention is to provide a medium for therapeutic plasma exchange that eliminates the risk of transmitting infectious viruses and leaves the plasma-protein profile of the patients treated practically unchanged.

This object is attained in accordance with the invention by means of a sterile plasma-exchange medium that contains the most essential human serum proteins, except for the coagulation factors, at a concentration of 75 g/l.

The most essential human serum proteins in the plasma-exchange medium in accordance with the invention are preferably albumin, the immunoglobulins IgG, IgA, and IgM, the inhibitors antithrombin III, $\alpha_1$-antitrypsin, and $\alpha_2$-macroglobulin, and complement C3.

The plasma-exchange medium in one especially preferred embodiment of the invention contains

| 35 to 50 | g/l of | albumin, |
| 6 to 12 | | IgG, |
| 1.0 to 2.5 | | IgA, |
| 0.5 to 2.5 | | IgM, |
| 10 to 80% | | normal antithrombin III |
| 0.1 to 0.3 | g/k of | $\alpha_1$-antitrypsin, |
| 0.1 to 0.3 | | $\alpha_2$-macroglobulin, and |
| 0.05 to 0.15 | | complement C3, | with the total concentration of serum proteins being 75 g/l. The sterile plasma-exchange medium in accordance with the invention can be prepared for example by concentrating a serum-protein solution sterilized with β-propriolactone and ultraviolet radiation as described in European Patent No. 0 014 333.

The present invention is based on the surprising discovery that using a serum-protein solution with a concentration 25 g/l higher than that of the known 5.0% solution in therapeutic plasma exchange will lead to no change worth mentioning in the protein profile of the people being treated. Comparison of an albumin solution (protein level of 50 g/l), the known serum-protein solution (protein level of 50 g/l), and the serum-protein solution in accordance with the invention (protein level 75 g/l) in a plasma exchange conducted in five healthy volunteers shows that increasing the concentration of the serum-protein solution from a protein level of 50 g/l to 75 g/l makes it possible to deceive the organism to an astonishing extent. The organism responds to a plasma exchange with the 5.0% serum-protein solution just as it does, though in a diminished form, to an exchange involving the 5.0% albumin solution, specifically with an attempt to restore the initial concentration of proteins by means of a hunting reaction—with the normal concentration initially either not being attained or being exceeded subsequent to the exchange. This restoration can take days or weeks. It is on the other hand surprisingly possible to avoid this reaction on the part of the organism in a plasma exchange that employs the plasma-exchange medium in accordance with the invention—the serum-protein solution with a protein level of 75 g/l.

The invention derives from the surprising results of a study involving a 75% plasma exchange carried over an interval of several months on 5 healthy volunteers with an albumin solution (5.0%), the known serum-protein solution (5.0%), and the plasma-exchange medium in accordance with the invention—a serum-protein solution with a protein level of 75 g/l. Serum or plasma had been obtained from the subjects participating in the study prior to the plasma exchange at intervals of 5 days for a total of 60 days to determine the control levels.

A mean was constructed from the results of the individual tests of the sera or plasmas from the 5 subjects per exchange group to make it possible to compare the results from this study of three different media in a therapeutic plasma exchange. Thus, the results for a specific protein per group could be plotted as a curve.

FIGS. I through IV are graphs using identical means to represent the results for each protein. The 60-day chronological axis is divided into intervals. The point at which the albumin was substituted in the group treated with the albumin solution is apparent (FIG. I) from the immediate rise in albumin concentration subsequent to the exchange, whereas the level initially drops to some extent in the group treated with the 5.0% serum-protein solution. Infusion of the 7.5% serum-protein solution in accordance with the invention, however, leads to such moderate alterations that deviations from the normal diurnal variations cannot be distinguished.

The immunoglobulins IgG, IgA, and IgM and the inhibitors $\alpha_1$-antitrypsin, $\alpha_2$-macroglobulin, and antithrombin III in the 5.0% serum-protein solution prevent, subsequent to plasma exchange with that solution, the concentrations of those proteins from decreasing to the extent that they do subsequent to albumin exchange. Exchange with the 5.0% serum-protein solution leads to much less extensive deviations in relation to restoration of the normal plasma-protein profile than in the case of albumin.

The surprising finding of the plasma-exchange study with respect to the 7.5% serum-protein solution is that increasing the protein concentration of the exchange medium from 50 to 75 g/l leads to restoration of the normal protein profile within a very short time subsequent to exchange. On the basis of the results of the study of the 5.0% serum-protein solution it would have been expected that an exchange carried out with the same protein solution but with the overall protein concentration increased from 50 to 75 g/l would necessarily lead to the protein profile familiar from exchange with the 5.0% serum-protein solution. After all, the two solutions contain the same proteins. Since then, both the 5.0% serum-protein solution and the 7.5% serum-protein solution in accordance with the invention contain exactly the same proteins, just the infusion of different amounts of the 5.0% serum-protein solution should have led to different protein profiles. This, however, did not occur. Surprisingly, then, the particular protein profile that occurs subsequent to plasma exchange does not depend on the number and amount of proteins infused with the exchange medium, but specifically, and in accordance with the invention, on the particular concentration of proteins in the plasma-exchange medium (cf. FIGS. I-IV).

Study of the profile of one protein, Factor VIII, as a function of the particular exchange medium employed reveals several surprising results. The Kotitschke et al long-term study previously cited herein contains two observations that can be considered surprising. The first is the different behaviors involved in readjusting the blood-coagulating Factors VIII and IX to their normal levels as a function of the exchange medium. The second is the time involved in this process subsequent to exchange with albumin.

Comparing the restoration of normal protein concentrations as a function of the plasma-exchange medium shows that the reaction on the part of the organism in attempting to attain that equilibrium depends on the extent of deviation from the normal state. If the deviation is very wide, as in albumin exchange for example, the reaction will be severe and will lead to the dramatic changes in Factor VIII concentrations for instance observed subsequent to exchange (FIG. IV). Since neither albumin nor the 5.0% serum-protein solution contain coagulation factors, a corresponding reaction can be assumed in relation to restoration of the initial concentrations of those proteins subsequent to exchange with both these media. The levels of Factors I and VIII actually detected, however, refute that assumption. The behavior subsequent to exchange with the 7.5% serum-protein solution in accordance with the invention must be considered surprising in comparison with the restoration of the concentration of Factor VIII subsequent to exchanges with albumin and with the 5.0% serum-protein solution because the phenomena of hunting the normal concentration of the protein is absent subsequent to plasma exchange with the 7.5% solution. Exchange with the medium in accordance with the invention, rather, leads only to brief inability to attain normal concentration subsequent to exchange, and not to exceeding it. The increasingly close approximation of the concentration of Factor VIII to normal surprisingly corresponds to what has been discovered with respect to all the other proteins. The peculiarities that occurred in relation to the Factor VIII protein profile subsequent to exchange with albumin and with the 5.0% serum-protein solution do not occur subsequent to exchange with the 7.5% serum-protein solution (FIG. IV).

The differences between the protein profiles established analytically in consequence of the different plasma-exchange media and illustrated for the different proteins in FIGS. I through IV are impressive even in the macroscopic finding represented by the plasma samples obtained at different points of time subsequent to plasma exchange. Some of these samples, obtained subsequent to plasma exchange with albumin, were coagulated. The number of coagulated plasma samples is represented by the Arabic numerals entered by way of illustration along the fibrinogen curve in FIG. IV. These findings confirm those cited for the risk of thrombosis in patients treated with repeated plasma exchanges with albumin solutions. A weighted hemostasis potential is necessary to avoid this risk of thrombosis. It must in particular include sufficient inhibitor potential to prevent an overload of procoagulation activities. Especially beneficial in plasma exchanges accordingly are media that supply enough inhibitors to prevent the risk of thrombosis. The effectiveness of the inhibitors in the plasma-exchange medium in accordance with the invention will be evident from the example of $\alpha_1$-antitrypsin in FIG. III. Another decisive advantage of the 7.5% serum-protein solution in accordance with the invention as a plasma-exchange medium in comparison with the 5.0% albumin solution is that it does not result in any depletion of the immunoglobulins as a result of plasma exchange and accordingly avoids the risk of the patients suffering from infections. Although this advantage is shared by the 5.0% serum-protein solution, Figure II shows that the 7.5% serum-protein solution in accordance with the invention has quantitative advantages that the 5.0% serum-protein solution lacks in that the normal IgG concentration is restored within 1 day of the plasma exchange.

The preparation of the plasma-exchange medium in accordance with the invention will now be described in the following illustrative example.

EXAMPLE 9 parts of donated venous blood were added to 1 part of a 3.8% sodium-citrated stabilizer solution. The blood was centrifuged as soon as possible subsequent to collection and the erythrocytes suspended in a physiological salt solution and reinfused into the donors. The plasma was frozen at $-40°$ C. within 48 hours.

The frozen plasma was thawed at a temperature of from $+2$ to $4°$ C. The cryoprecipitate was centrifuged out.

The cryoprecipitate-free citrated-plasma pool was treated at room temperature with freshly distilled $\beta$-propriolactone to a concentration of 0.25% by volume. It was stirred at room temperature for 1 hour while being maintained at a pH of 7.2 by the continuous addition of 1N sodium hyroxide solution. Subsequent to ultraviolet irradiation with a continuous-flow apparatus (Dill) the $\beta$-propriolactone was hydrolyzed by the continuous addition of 1N sodium hydroxide solution, with the pH being maintained constant up to the end, until the pH remained constant with no more sodium hydroxide being added. The citrated plasma, treated with $\beta$-propriolactone and irradiated with ultraviolet light, was chilled to $4°$ C. and adsorbed, at a pH of 7.2 and while being stirred, with 0.5 g of DEAE Sephadex A 50 ® (diethylaminoethyl Sephadex, Pharmacia Fine Chemicals' trade name for a dextran cross-linked with epichlorohydrin).

The plasma remaining subsequent to the DEAE-Sephadex adsorption was adsorbed for 3 hours at $+45°$ C. with 3% colloidal silicic acid and centrifuged to remove the silicic acid. The resulting solution was clarified on hot-air sterilized membranes with a pore size of 5 $\mu$m.

To decrease the levels of silicate, calcium, and phosphate in the clarified solution it was filtered through ultrafiltration cartridges (Amicon PM 10) at approximately $+20°$ C. The resulting solution was concentrated to a protein concentration of 75 g/l. Appropriate salts were added to adjust the electrolytes to the desired concentrations. This protein solution, ultrafilterd, concentrated, and adjusted to the desired electrolyte concentration, was then decanted into empty, sterile 1-liter flasks through hot-air sterilized membrane filters with pore sizes of 0.45 and 0.22 $\mu$m.

The table illustrates the composition and properties of the resulting 7.5% serum-protein solution.

TABLE

| Composition and properties of the 7.5% serum-protein solution | | | |
|---|---|---|---|
| Protein (g/l) | 75 | Electrolytes | |
| Albumin (g/l) | 45–50 | $Na^+$ (meq/l) | 144–170 |
| IgG (g/l) | 9–10 | $K^+$ (meq/l) | 3.1–4.7 |
| IgA (g/l) | 1.7–2.0 | $Ca^{++}$ (meq/l) | 2.6–5.6 |
| IgM (g/l) | 0.7–1.0 | $Cl^-$ (meq/l) | 109–191 |
| Antithrombin III (% norm.) | 25–40 | $Mg^{++}$ (meq/l) | 1.7–2.3 |
| $\alpha_1$-Antitrypsin (g/l) | 0.2–0.25 | Citrate (meq/l) | 15–25 |
| $\alpha_2$-Macroglobulin (g/l) | 0.2–0.25 | Phosphate (meq/l) | 1.0–2.0 |
| Complement C3 (g/l) | 0.1–0.12 | Silicate (meq/l) | <15.0 |
| Cholinesterase (U/l) | ≈200 | Hb (g/l) | <0.05 |
| Total lipids (g/l) | <0.05 | Iron (μg/dl) | 140–180 |
| Cholesterol (g/l) | <0.05 | | |
| Glucose (g/l) | <0.05 | PKA (% norm.) | negative |
| Cellulose-acetate film electrophoresis | | | |
| Albumin (rel. %) | 60–70 | Anti-A (titer) | ≦1:64 |
| $\alpha_1$ Proteins | 3–4 | Anti-B (titer) | ≦1:64 |
| $\alpha_2$ Proteins | 8–11 | HBsAg | negative |
| $\beta$ Proteins | 8–11 | KBR (Ch 50/mg) | >0.4 |
| $\gamma$ Proteins | 11–16 | | |
| Bacterial-activity titers | | Viral-activity titers | |
| *E. coli* | 1:80 | Herpes 1 | 1:5 |
| *Ps. aeruginosa* | 1:160 | Herpes 2 | 1:5 |
| Klebs. | 1:40 | VZV | 1:5 |
| Staph. | 1:40 | CMV | 1:5 |
| *Str. haem.* | 1:40 | Rubella | 1:64 |
| *Str. virid.* | 1:20 | | |

It will be understood that the specification and examples are illustrative but not limitative of the present invention and that other embodiments within the spirit and scope of the invention will suggest themselves to those skilled in the art.

I claim:

1. In the replacement of a patient's plasma with a substitute medium, the improvement which comprises employing as such substitute medium a sterile plasma-exchange medium containing the most essential human serum proteins, wherein said medium does not contain the blood coagulation factors at a concentration of about 75 g/l, and wherein said most essential human serum proteins comprise:

| | |
|---|---|
| 10 to 80% | normal blood content of antithrombin III, and |
| 35 to 50 | g/l of albumin, |
| 6 to 12 | g/l of IgG, |
| 1.0 to 2.5 | g/l of IgA, |
| 0.5 to 2.5 | g/l of IgM, |
| 0.1 to 0.3 | g/l of $\alpha_1$-antitrypsin, |
| 0.1 to 0.3 | g/l of $\alpha_2$-macroglobulin, and |
| 0.05 to 0.15 | g/l of complement C3. |

* * * * *